(12) United States Patent
Cheng et al.

(10) Patent No.: US 9,535,057 B2
(45) Date of Patent: *Jan. 3, 2017

(54) METHOD OF IN VIVO SCREENING FOR CARDIAC TOXIC AGENTS USING TELEOST

(75) Inventors: Shuk Han Cheng, Kowloon (HK); Po Kwok Chan, Tseung Kwan O (HK)

(73) Assignee: CITY UNIVERSITY OF HONG KONG, Hong Kong (CN)

(*) Notice: Subject to any disclaimer, the term of this patent is extended or adjusted under 35 U.S.C. 154(b) by 737 days.

This patent is subject to a terminal disclaimer.

(21) Appl. No.: 12/224,577

(22) PCT Filed: Jan. 8, 2007

(86) PCT No.: PCT/CN2007/000035
§ 371 (c)(1),
(2), (4) Date: Aug. 29, 2008

(87) PCT Pub. No.: WO2008/086646
PCT Pub. Date: Jul. 24, 2008

(65) Prior Publication Data
US 2009/0232739 A1    Sep. 17, 2009

(51) Int. Cl.
*G01N 33/50* (2006.01)

(52) U.S. Cl.
CPC ...... *G01N 33/5088* (2013.01); *G01N 33/5014* (2013.01); *G01N 2333/4603* (2013.01); *G01N 2800/326* (2013.01)

(58) Field of Classification Search
CPC ............ A01K 2267/03; G01N 33/5014; G01N 2333/4603;G01N 2333/505; G01N 33/5088

See application file for complete search history.

(56) References Cited

U.S. PATENT DOCUMENTS

| | | | |
|---|---|---|---|
| 2003/0161787 A1* | 8/2003 | Lanheinrich | 424/9.2 |
| 2004/0133114 A1 | 7/2004 | MacRae et al. | |
| 2004/0143865 A1 | 7/2004 | Rubinstein et al. | |
| 2006/0018833 A1 | 1/2006 | Murphy et al. | |

FOREIGN PATENT DOCUMENTS

WO    WO 03/008633    1/2003

OTHER PUBLICATIONS

Schwerte (Comparative Biochem and Physiol Part A. 2003. 135:131-143).*
Schwerte et al., (J Exp Biol. 2000. 103, 1659-1669).*
Schwerte et al., (J Exp Biol. Mar. 2006;209(Pt. 6):1093-1100).*
LeMevel et al., (Brain Research. 2002:947;34-40).*
Cheng, Shuk Han et. al., "The use of microangiography in detecting aberrant vasculature in zebrafish embryos exposed to cadmium," Aquatic Toxicology (2001) vol. 52, pp. 61-71.

(Continued)

*Primary Examiner* — Cherie M Stanfield
(74) *Attorney, Agent, or Firm* — Andrews Kurth Kenyon LLP

(57) ABSTRACT

This invention relates to a method of screening agents for cardiotoxicity based on the observations of the alteration of heart rate and heart rhythm, using teleost embryos and larvae. This invention also relates to a method for identification of gene(s) related to cardiac functions in teleost.

9 Claims, 5 Drawing Sheets

(56) References Cited

OTHER PUBLICATIONS

Colman, J.R. et. al., "Teratogenic effects of azaspiracid-1 identified by microinjection of Japanese medaka (*Oryzias latipes*) embryos," Toxicon (2005) vol. 45, pp. 881-890.

Schwerte, T. et. al., "Epigenetic variations in early cardiovascular performance and hematopoiesis can be explained by maternal and clutch effects in developing zebrafish (*Danio rerio*)," Comparative Biochemistry and Physiology Part A (2005) vol. 141, pp. 200-209.

Schwerte, T., et. al., "Understanding cardiovascular physiology in zebrafish and Xenopus larvae: the use of microtechniques," Comparative Biochemistry and Physiology Part A (2003), vol. 135, pp. 131-145.

Zhang, L., et. al., "The effect of exogenous retinoic acid on the cardiovascular development of zebrafish embryos," ACTA Laboratorium Animalis Scientia Sinica, (Jun. 2006), vol. 14(2), pp. 84-88 [English-language abstract provided herewith].

Chan, P. K. et al., "Nonivasive technique for measurement of heartbeat regularity in zebrafish (*Danio rerio*) embryos," BMC Biotechnology (2009), vol. 9:11, 10 pages.

Langheinrich, U et al., "Zebrafish embryos express an orthologue of HERG and are sensitive toward a range of QT-prolonging drugs inducing severe arrhythmia," Toxicology and Applied Pharmacology (2003), vol. 193:3, pp. 370-382.

Schwerte, T. et al., "Development of the sympatho-vagal balance in the cardiovascular system in zebrafish (*Danio rerio*) characterized by power spectrum and classical signal analysis," The Journal of Experimental Biology (2006), vol. 209:6, pp. 1093-1100.

Supplementary European Search Report and Opinion from related EP Application No. 07701967.

International Preliminary Report on Patentability from International Patent Application No. PCT/CN2007/000035.

\* cited by examiner

METHOD OF IN VIVO SCREENING FOR CARDIAC TOXIC AGENTS USING TELEOST

FIELD OF THE INVENTION

Cardiac arrhythmia, a group of conditions in which the heart beat is going too fast (tachyrhythmia), too slow or irregularly (bradyrhythmia), is a life-threatening medical emergency that causes cardiac arrest and sudden death (Kleber and Rudy. 2004). The common causes for both congenital and acquired cardiac arrhythmia are genetic and chemical- or disease-induced perturbations of cardiac rhythm. Over 50 therapeutic compounds have shown the potential to induce unexpected cardiac arrhythmia and some of them were withdrawn from market. Cardiac arrhythmia is now considered a significant risk factor for predicting human safety of new therapeutic compounds. Therefore, drug regulatory authorities now have increased concerns regarding arrhythmic potential of therapeutic compounds and regulatory advice on evaluation of promoting arrhythmia has been issued (Stockbridge and Throckmorton. 2004).

BACKGROUND OF THE INVENTION

Cellular electrophysiological basis for cardiac arrhythmia is due to blockage of ion channels, resulting in delay of repolarization and prolongation of QT interval, characteristics of ECG with longer interval between Q and T points (Keating and Sanguinetti. 2001; Roden et al. 2002). Because it is the target of most non-cardiac drugs that cause cardiac arrhythmia (Abriel et al. 2004; Joshi et al. 2004), special attention is paid to hERG (human ether-à-go-go-related gene) which encodes for the pore-forming α subunit of the rapidly activating delayed rectifier potassium channel. The channel is responsible for the repolarizing potassium current which is distinguished from other current by strong inward rectification. Inhibition of this channel, either by exogenous compounds or due to genetic mutation, increases the duration of repolarization of action potential in cardiac myocytes, resulting in cardiac arrhythmias. Nevertheless, cardiac arrhythmia is not only due to the malfunction of hERG but also other ion channels, such as sodium channels and calcium channels. Thus, emphasis is put on the preclinical screening for new therapeutic compounds with any unexpected cardiac toxic effects by highly sensitive and specific experimental models (Joshi et al. 2004).

Traditionally, patch clamp electrophysiology is regarded as the "gold standard" for measuring of ion channel activity (Fermini and Fossa. 2003). Patch clamp allows for the direct and real-time monitoring of ion channel activity in the administration of testing compounds in whole-cell mode. However, it is a low-throughput methodology and requires highly skillful operators. Although other advanced screening technologies have been developed recently to improve the degree of throughput, all these technologies are based on in vitro cell culture models. The disadvantage of using in vitro model is that complex physiological environment that occurs in vivo cannot be modeled in an in vitro system. Some biological questions of cardiac electrophysiology cannot simply be addressed by in vitro assays. In this case, in vivo models have been applied, including Guinea pig, dog, and primate. ECG is continuously recorded over a range of increasing doses in anaesthetized animal to detect the occurrence of any cardiac arrhythmia. Moreover, they are not widely used due to the ethical issues and cost efficiency. Therefore, there is a need to develop a new technology with lower cost and higher efficiency.

Zebrafish has emerged as a model in developmental biology studies, toxicology studies as well as pharmaceutical studies. Zebrafish in vivo bioassay combines the advantages of high throughput, as compared to mammalian in vivo assays, and high relevance, as compared to in vitro assays. Recently, two articles have been published demonstrating similar physiological responses of zebrafish to well-know compounds that induce cardiac arrhythmia in humans (Langheinrich et al. 2003; Milan et al. 2003). Furthermore, the ortholog of hERG was cloned and showed high similarity in protein sequence in the pore region and the cyclic-nucleotide binding region to which some cardiac toxic compounds bind (Langheinrich et al. 2003). In addition, mutation in zERG exhibits similar phenotype of cardiac arrhythmia as in human. These results suggest zebrafish may be used as a model for screening compounds with cardiac toxicity.

Methods have been developed to measure cardiac function in zebrafish. However, they are usually low throughput, time consuming and labor intensive. The simplest method is to use a stopwatch to count number of heart beat per minute under conventional light microscope or stereomicroscope (Langheinrich et al. 2003). An image analysis method of digital movie of heart has been developed (Milan et al. 2003). Average pixel intensity of a particular region of heart was measured. Fast Fourier transform of these data was performed to determine the heart rate. Beside heart rate, other cardiac parameters, e.g. cardiac output, hemodynamics and electrical properties, have been developed (reviewed by (Schwerte and Fritsche. 2003)). Cardiac output, an important parameter of cardiac physiology, can be determined non-invasively in transparent zebrafish embryos by calculation of the ventricular volume during cardiac cycle by filming the beating ventricle. The formula of volume calculation requires the length of axes of ventricle which can be obtained by outlining the ventricle manually or automatically with the assistance of a computer program. Hemodynamics as determined by blood pressure can be measured using servo-null micropressure system. In the system, a glass capillary filled with a NaCl solution of high concentration is inserted into the blood vessels of interest using a micromanipulator. Pressure change in the blood vessel will move the interface between the plasma and NaCl solution, resulting in the change of electrical resistance of the electrode inside the glass capillary. Recently, methodology for measuring electrical properties in zebrafish embryos has been developed (Forouhar et al. 2004). In the methodology, five day old embryos are mounted on their dorso-ventral orientation and two electrodes are positioned using a micromanipulator, one on the body surface outside the heart and another reference electrode in the surrounding solution. However, these methods are also time-consuming and labor intensive, particularly in sample preparation steps, making them not suitable for high throughput study.

SUMMARY OF THE INVENTION

The invention relates to a method of using a teleost as model to screen agents for cardiotoxic effect, particularly alteration in heart rate and in heart beat rhythm. Teleosts, either embryos or larvae, are bathed in medium containing testing agents for a particular period of time. Then, the teleost is immobilized by agarose, agar or methyl-cellulose. Circulation of blood cells are videoed under microscope equipped with digital camera connected to a recording device, such as a VCR recorder, digital video camera or personal computer. Video of blood circulation is then analyzed by image analyzing software using a video image analysis method in which moving blood cells within each video frame are detected and quantified. A series of data points is obtained from each video frame from a part of the video or from the whole video. Power spectral analysis is then applied to analyze the series of data points, by which heart rate and quantitative parameter of heart beat rhythm are obtained. Our experimental results showed that the heart rate calculated by the present invention is equivalent to the heart rate determined by direct examination of heart. Furthermore, our results also showed that the quantitative parameter of heart beat rhythm, the cardiac rhythmicity index calculated by the present invention, is inversely correlated with the regularity of heart beat rhythm.

DETAILED DESCRIPTION OF THE INVENTION

The present invention describes a method of using a teleost to screen agents with any cardiotoxic effect, particularly alteration in heart rate and in heart beat rhythm.

The teleost can be an embryo or larvae of any fish belonging to the subclass Teleostomi, preferably, for example zebrafish and medaka because they offer advantages of external fertilization and transparency over other animal model used in cardiotoxicity assays.

Exposure of agents to teleosts can be started from the time of fertilization or started at a particular time after fertilization. The length of exposure can be covered from the beginning of exposure to the time of examination or within a particular length of exposure time followed by a period of recovery time during which the teleost is bathed in medium without a testing agent. An agent can be dissolved in water or medium used to bathe the teleost. Alternatively, an aqueous-insoluble agent can be dissolved in DMSO in high concentration and, during exposure, added to bathing medium directly.

Before videoing blood cell circulation, the teleost is immobilized on a surface, for example, glass slide or plastic petri dish. Immobilization medium can be agarose, agar or methyl-cellulose. The optimal concentration of agarose or agar used is 0.5% (w/v) or lower. The concentration of methyl-cellulose used is 2-4% (w/v). Teleosts should be oriented in their spontaneous lateral position. Preferably, circulation in tail posterior part of teleost is ideal for the analysis of cardiotoxicity in the present invention.

Figure 1:
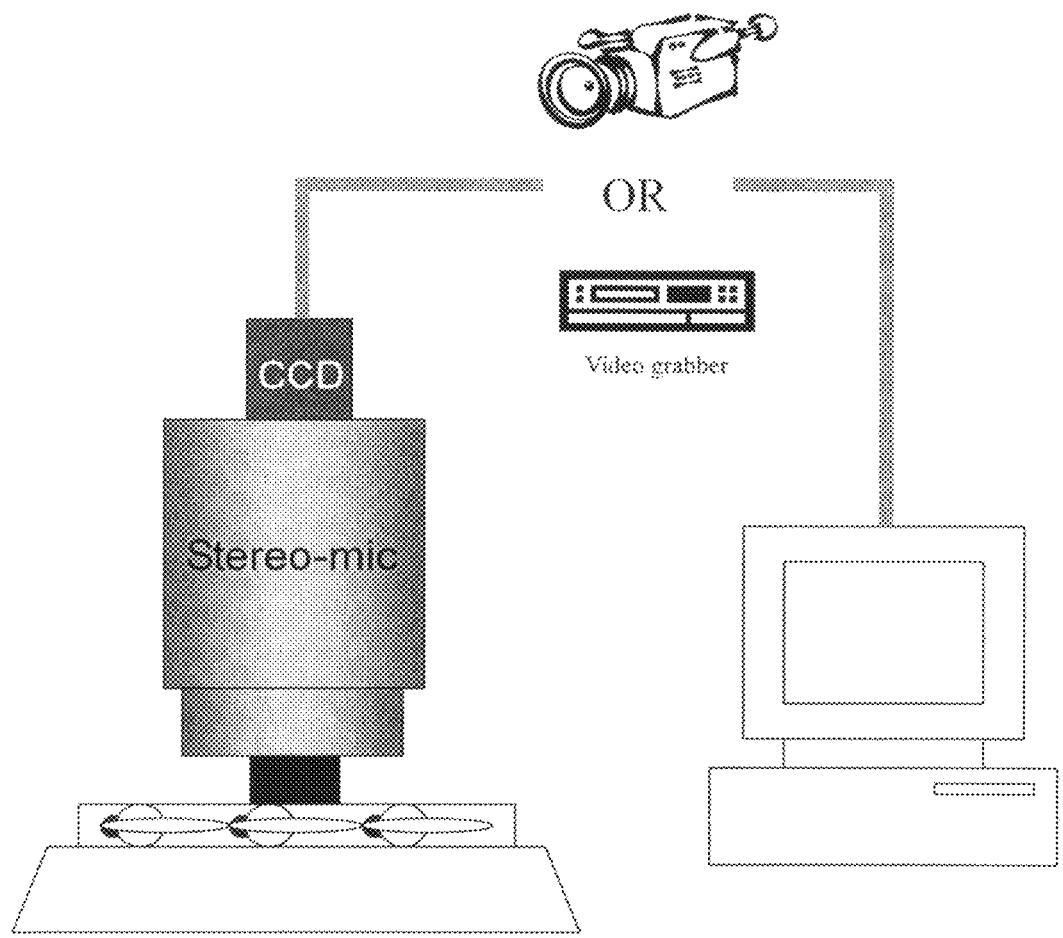
FIG. 1 Schematic diagram of imaging system.

A video imaging system consists of a microscope, either stereomicroscope or conventional light microscope, with low magnification objective (FIG. 1). The microscope is connected with a camera, either analog or digital, connected to a recording device, such as a VCR recorder, digital video camera or personal computer with video frame grabber. Video recorded in medium, e.g. VCR tape or mini DV tape, or recorded in personal computer is converted back to readable format, such as AVI or WMV format, and stored in personal computer for further video image analysis. The length of video for each teleost sample should not be less than 20 seconds.

Figure 2:
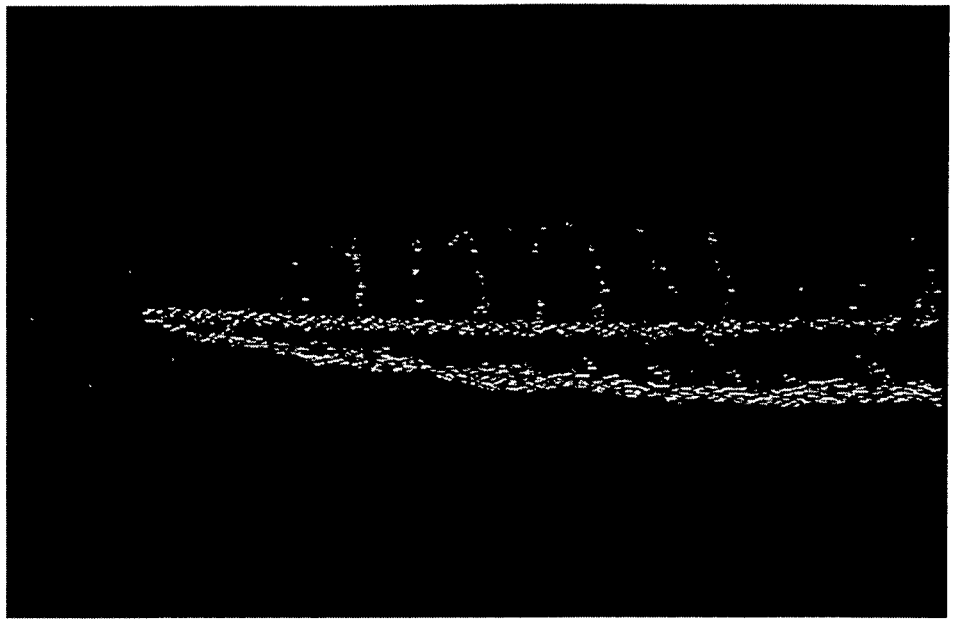
FIG. 2 Example of image subtraction result.
Figure 3:
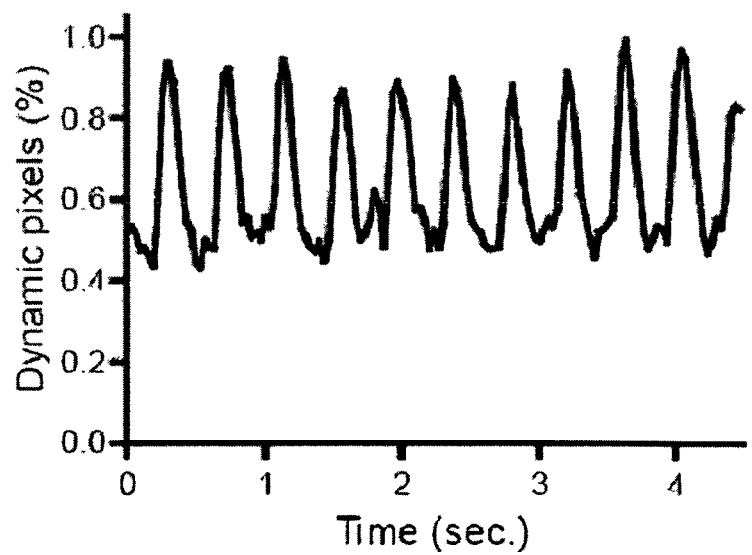
FIG. 3 Plot of differential pixels for the duration of 4 seconds.

Subsequent video image analysis is performed by a novel algorithm implemented in a home-made software. In the algorithm, a video frame is grabbed from the video file stored in personal computer, either in AVI or WMV format and immediately subtracted with its consecutive video frame. The subtraction is performed in pixel intensity value in pixel-by-pixel manner. Any movement that occurred between two consecutive video frames will lead to a difference in the pixel intensity. Thus, subtraction will reveal moving blood cells in the video. A sample subtraction result is shown in FIG. 2. Since the time interval between each video frame is constant and the amount of differential pixels is related to the distance traveled by the blood cells between two video frames, the amount of differential pixels can be used to estimate the speed of blood cells. Plotting the amount of differential pixels, i.e. pixels with different pixel intensity to the corresponding pixel in the consecutive video frame, against time in seconds exhibits a wave-form curve with regular oscillation (FIG. 3), suggesting the oscillation in the blood cells speed.

Figure 4:
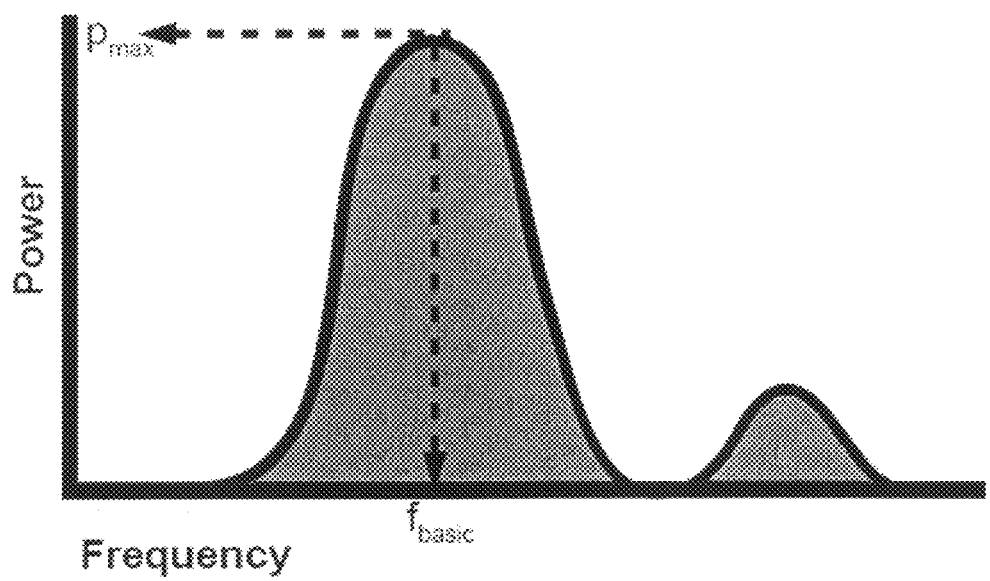
FIG. 4 Schematic diagram illustrating the identification of basic frequency component and its peak power value, and the calculation of total power.

Data analysis of the series of the amount of differential pixels obtained from video image analysis is performed by methods implemented in the home-made software. Data series of amount of differential pixels is analyzed by comprising power spectral analysis in which data series of differential pixels is decomposed by discrete Fourier transform. A discrete Fourier transform algorithm (Ferguson. 1979) is used. A power spectrum is obtained by autocorrelation of the Fourier series and is plotted against the frequency values (FIG. 4). A total power value of the spectrum is calculated. The highest peak with lowest frequency value ($p_{max}$) is defined as the basic frequency component of the input signal. The frequency value is equivalent to the heart rate. The ratio of highest peak value to the total power value serves as the cardiac rhythmicity index. The principle of the calculation is that when the input signals with frequencies varying around the basic frequency component, the peak of basic frequency component in its power spectrum will be lower with frequency components around it higher. Thus, the ratio of basic frequency component power to total power decreases.

Figure 5:
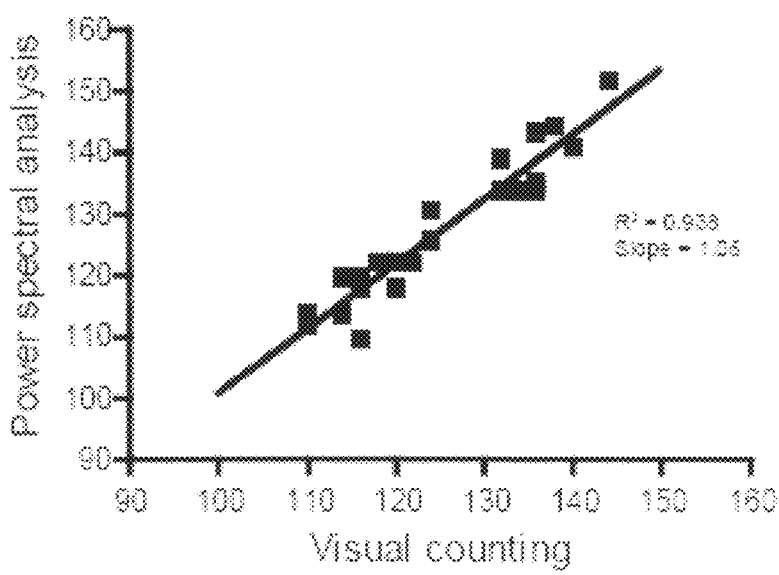
FIG. 5 Correlation of heart rate determined from heart and tail circulation by power spectral analysis.
Figure 6:
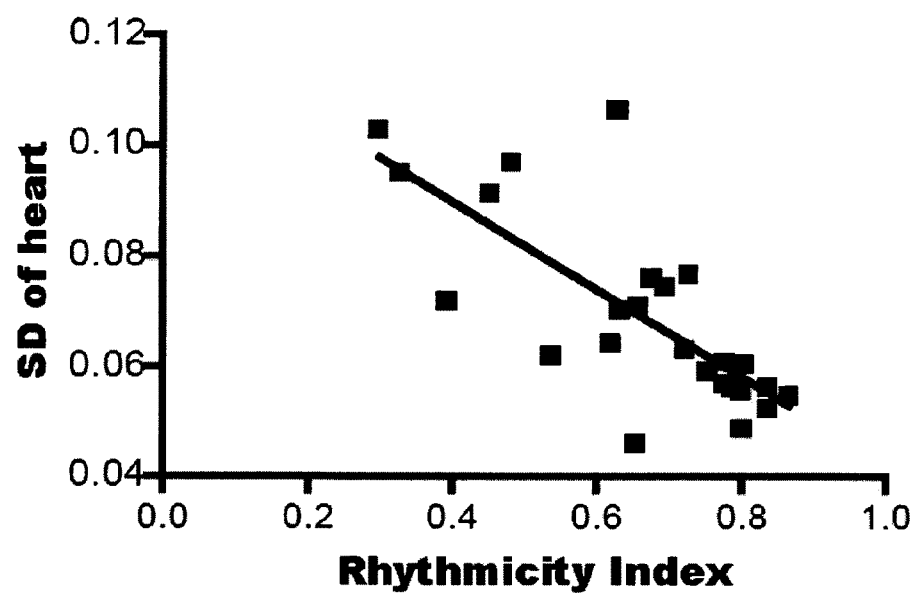
FIG. 6 Correlation of cardiac rhythm and the rhythmicity index determined by power spectral analysis.

The embodiment is tested in wild type embryos at 52 hpf. Videos of heart and tail circulation are taken for analysis. Heart rate is determined from direct visual counting of the number of heart beats in 1 min. In addition, heart rate is calculated by the multiplication of basic frequency component in power spectrum with 60. Calculated heart rate is correlated with the heart rate determined by direct examination of heart (FIG. 5). In addition, the cardiac rhythm is determined as the standard deviation of heart beat time interval. If the heart beat is irregular, the standard deviation of heart beat time interval will be increased. The cardiac rhythmicity index is calculated as the ratio of power value of basic frequency value to the total power value of whole spectrum. The cardiac rhythmicity index is inversely correlated with the standard deviation of heart beat time interval determined by direct examination of heart (FIG. 6), suggesting that the larger the rhythmicity index the more regular the heart beat rhythm.

EXAMPLES

This example illustrates the use of the present invention to determine the heart rate and the cardiac rhythmicity index in zebrafish larvae exposed to well-known human cardiac arrhythmia inducing drug, haloperidol. Haloperidol is a butyropherone derivative with antipsychotic properties. Cardiac arrhythmia has been related to the oral use of haloperidol (Henderson et al. 1991) and the mechanism of haloperidol-induced arrhythmia involved the blockage of hERG channel (Suessbrich et al. 1997).

Stock solution of haloperidol was prepared by dissolving it in DMSO in final concentration of 2 mM. Zebrafish eggs are collected and placed in egg medium (19.3 mM NaCl, 0.23 mM KCl, 0.13 mM $MgSO_4 \cdot 7H_2O$, 0.2 mM $Ca(NO_3)_2$, 1.67 mM Hepes (pH 7.2) at 28.5° C. for 4 hours before sorting for viability. Healthy embryos are then incubated at 28.5° C. up to 48 hpf. Six µl of stock solution was added to 6-ml egg medium containing 20 healthy 48-hpf embryos. The final concentration of haloperidol is 2 µM and the final concentration of DMSO was 0.1% at which no effect was observed in zebrafish. After 4 hour of incubation, blood circulation of zebrafish is examined and videoed under stereomicroscope equipped with CCD camera connected to digital video camera via S-video cable. Video is stored in mini DV tape and transferred back to personal computer via the connection of i-Link between digital video camera and computer. Video clip is stored in personal computer in the format of AVI. Image analysis and data analysis is performed by our home-made software implemented algorithms of image analysis and data analysis.

Figure 7:
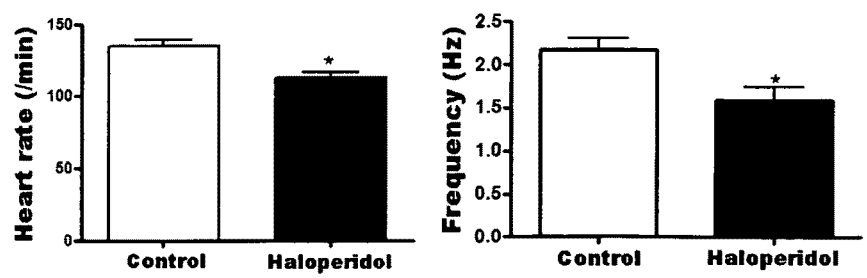
FIG. 7 Comparison of haloperidol-induced heart rate alteration determined by direct examination of heart and power spectral analysis. Asterisk indicates the statistically significant difference between control group and haloperidol group ($p<0.05$).
Figure 8:
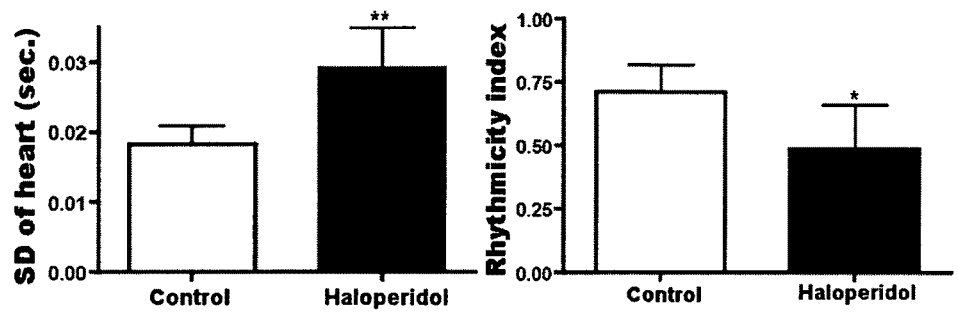
FIG. 8 Comparison of haloperidol-induced heart beat rhythmicity alteration determined by direct examination of heart and power spectral analysis. Asterisk indicates the statistically significant difference between control group and haloperidol group ($p<0.05$) while double asterisks indicate the statistically significant difference between control group and haloperidol group ($p<0.01$).

After treatment of haloperidol, the heart rate is significantly decreased (FIG. 7), similar to published data (Langheinrich et al. 2003; Milan et al. 2003). In addition to the heart rate, we also analyze the rhythmicity of heart beat after haloperidol treatment, which is not published in any paper assessing cardiac function in zebrafish embryos. The standard deviation of time interval taken between each heart beat determined by direct examination of heart is increased (FIG. 8). At the same time, the cardiac rhythmicity indices in treated embryos are decreased (FIG. 8).

The invention claimed is:

1. A method of screening agents for the ability to alter heart rate and regularity of heart beat rhythm, which comprises:
    a. incubating a transparent embryo or larva of a teleost in medium containing testing agent;
    b. optionally, immobilizing said embryo or larva on a surface;
    c. videoing the circulation of blood cells of said embryo or larva under a microscope equipped with a camera connected to a recording device; and
    d. analyzing the video with image analysis software in which moving blood cells within each video frame are detected and quantified, in order to obtain a series of data points from each video frame from either a part of the video or the whole of the video;
    e. applying power spectral analysis to analyze the series of data points, in order to obtain a cardiac rhythmicity index;

wherein the cardiac rhythmicity index is inversely correlated with the regularity of heart beat rhythm.

2. The method of claim 1, wherein said embryo or larva is from zebrafish or medaka.

3. The method of claim 1, wherein the embryo or larva comprises fertilized eggs of at least 48 hours post fertilization.

4. The method of claim 1, wherein said embryo or larva in step (a) is incubated for at least 4 hours.

5. The method of claim 1, wherein step (b) comprises immobilization of teleost embryos or larvae in immobilization medium, such as agarose, agar or methyl-cellulose.

6. The method of claim 1, wherein step (c) comprises video recording of circulation of blood cells at any part of embryo or larvae body for at least 20 seconds.

7. The method of claim 1, wherein in step (c) the circulation of blood cells is videoed in the tail.

8. The method of claim 1, wherein the video analysis method is capable of quantifying the speed of the blood cells by calculating the distance the blood cells traveled during the analyzing time interval.

9. The method of claim 1, wherein the cardiac rhythmicity index of step (e) is obtained by comparing the time intervals determined by power spectral analysis.

* * * * *